United States Patent
George et al.

(10) Patent No.: US 12,035,938 B2
(45) Date of Patent: Jul. 16, 2024

(54) SURGICAL ACCESS DEVICE WITH DETACHABLE FIXATION ASSEMBLY

(71) Applicant: Covidien LP, Mansfield, MA (US)

(72) Inventors: Sabastian Koduthully George, Hyderabad (IN); Oksana Buyda, East Haven, CT (US)

(73) Assignee: Covidien LP, Mansfield, MA (US)

( * ) Notice: Subject to any disclaimer, the term of this patent is extended or adjusted under 35 U.S.C. 154(b) by 406 days.

(21) Appl. No.: 17/153,982

(22) Filed: Jan. 21, 2021

(65) Prior Publication Data

US 2021/0290263 A1      Sep. 23, 2021

Related U.S. Application Data

(60) Provisional application No. 62/991,747, filed on Mar. 19, 2020.

(51) Int. Cl.
*A61B 17/34* (2006.01)

(52) U.S. Cl.
CPC .. *A61B 17/3423* (2013.01); *A61B 2017/3435* (2013.01); *A61B 2017/347* (2013.01)

(58) Field of Classification Search
CPC .......... A61B 17/3423; A61B 2017/348; A61B 2017/3482; A61B 2017/3484
See application file for complete search history.

(56) References Cited

U.S. PATENT DOCUMENTS

| | | | |
|---|---|---|---|
| 4,521,938 A * | 6/1985 | Kupcikevicius | ... A22C 11/0254 452/38 |
| 5,073,169 A | 12/1991 | Raiken | |
| 5,137,520 A | 8/1992 | Maxson et al. | |
| 5,176,648 A | 1/1993 | Holmes et al. | |
| 5,226,890 A | 7/1993 | Ianniruberto et al. | |
| 5,290,249 A | 3/1994 | Foster et al. | |
| 5,300,033 A | 4/1994 | Miller | |
| 5,330,497 A | 7/1994 | Freitas et al. | |
| 5,366,446 A | 11/1994 | Tal et al. | |
| 5,403,336 A | 4/1995 | Kieturakis et al. | |
| 5,484,420 A | 1/1996 | Russo | |

(Continued)

FOREIGN PATENT DOCUMENTS

EP      0589452 A1      3/1994

*Primary Examiner* — Nicholas W Woodall

(74) *Attorney, Agent, or Firm* — Carter, DeLuca & Farrell LLP

(57) ABSTRACT

A surgical access device includes a cannula assembly, a locking collar, a fixation sleeve assembly, and a tip portion. The cannula assembly includes a housing and a tubular member extending from the housing. The locking collar slidably is received on the tubular member. The fixation sleeve assembly is disposed about the tubular member. The fixation sleeve assembly includes a securing member configured to detachably engage the locking collar, and a sleeve extending distally from the securing member. The tip portion detachably is coupled to a distal portion of the tubular member to retain the fixation sleeve assembly on the tubular member. The fixation sleeve assembly is transitionable between a first configuration, in which, the sleeve has a tubular profile, and a second configuration, in which, the sleeve flexes radially outwards to define a fixation anchor configured to secure the surgical access device relative to an opening in tissue.

13 Claims, 4 Drawing Sheets

(56) References Cited

U.S. PATENT DOCUMENTS

| | | | |
|---|---|---|---|
| 5,713,869 A | 2/1998 | Morejon | |
| 5,792,112 A | 8/1998 | Hart et al. | |
| 5,830,232 A | 11/1998 | Hasson | |
| 6,451,041 B1 * | 9/2002 | Moenning | A61M 25/02 |
| | | | 604/164.04 |
| 6,908,454 B2 | 6/2005 | McFarlane | |
| 7,300,448 B2 | 11/2007 | Criscuolo et al. | |
| 7,316,699 B2 | 1/2008 | McFarlane | |
| 7,691,089 B2 | 4/2010 | Gresham | |
| 7,744,617 B2 | 6/2010 | Lunsford et al. | |
| 7,963,975 B2 | 6/2011 | Criscuolo | |
| 2004/0138702 A1 | 7/2004 | Peartree et al. | |
| 2005/0113856 A1 | 5/2005 | Epstein et al. | |
| 2005/0165432 A1 | 7/2005 | Heinrich | |
| 2006/0079918 A1 | 4/2006 | Creston | |
| 2006/0106402 A1 | 5/2006 | McLucas | |
| 2010/0063356 A1 * | 3/2010 | Smith | A61B 17/3415 |
| | | | 600/114 |
| 2011/0213317 A1 * | 9/2011 | Chen | A61F 9/007 |
| | | | 604/264 |
| 2019/0307486 A1 * | 10/2019 | Buyda | A61B 17/3462 |

\* cited by examiner

SURGICAL ACCESS DEVICE WITH DETACHABLE FIXATION ASSEMBLY

CROSS-REFERENCE TO RELATED APPLICATIONS

This application claims the benefit of and priority to U.S. Provisional Patent Application Ser. No. 62/991,747, filed Mar. 19, 2020, the disclosure of which is incorporated by reference herein in its entirety.

TECHNICAL FIELD

The present disclosure relates generally to a surgical access device, and, in particular, relates to an access device having a detachable fixation assembly to thereby minimize the potential of inadvertent removal of the surgical access device relative to the tissue site.

BACKGROUND OF RELATED ART

Minimally invasive surgical procedures including both endoscopic and laparoscopic procedures permit surgery to be performed on organs, tissues and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a surgical access device accessing the abdominal cavity to perform one or more surgical tasks. The surgical access device may incorporate a seal to establish a substantially fluid tight seal about the instrument to preserve the integrity of the pneumoperitoneum.

While minimally invasive surgical procedures have proven to be quite effective in surgery, several limitations remain. For example, the surgical access device which is subjected to the pressurized environment, i.e., the pneumoperitoneum, may have a tendency to back out of the incision in the abdominal wall particularly during multiple manipulations of the instrument within the surgical access device.

SUMMARY

In accordance with an aspect of the present disclosure, a surgical access device includes a cannula assembly, a locking collar, a fixation sleeve assembly, and a tip portion. The cannula assembly includes a housing and a tubular member extending from the housing. The cannula assembly defines a passage channel configured to receive a surgical instrument therethrough. The locking collar is slidably received on the tubular member of the cannula assembly. The fixation sleeve assembly is disposed about the tubular member of the cannula assembly. The fixation sleeve assembly includes a securing member configured to detachably engage the locking collar, and a sleeve extending distally from the securing member. The tip portion is detachably coupled to a distal portion of the tubular member of the cannula assembly to retain the fixation sleeve assembly on the tubular member of the cannula assembly. The fixation sleeve assembly is transitionable between a first configuration, in which, the sleeve has a tubular profile, and a second configuration, in which, the sleeve flexes radially outwards to define a fixation anchor configured to secure the surgical access device relative to an opening in tissue.

In an aspect, the locking collar may be disposed in a proximal portion of the tubular member when the fixation sleeve assembly is in the first configuration, and in a distal portion of the tubular member when the fixation sleeve assembly is in the second configuration.

In another aspect, the tubular member of the cannula assembly may include proximal and distal retaining features to retain the locking collar thereon.

In yet another aspect, the proximal and distal retaining features may frictionally engage the locking collar.

In still yet another aspect, the distal retaining feature may be disposed adjacent the tip portion.

In still yet another aspect, the locking collar may have an annular base and an annular flange extending radially outward from the annular base and proximal of the annular base.

In an aspect, the securing member of the fixation sleeve assembly may threadably engage threads on an outer surface of the annular base.

In another aspect, the fixation anchor may have a tapered configuration.

In yet another aspect, the tip portion may have an outer diameter greater than an inner diameter of the sleeve of the fixation sleeve assembly.

In still yet another aspect, the housing and the tubular member of the cannula assembly are integrally formed as a single construct.

In another aspect, the sleeve of the fixation sleeve assembly may include a braid, a weave, a mesh, a non-woven structure, a knitted structure, or a fabric.

In accordance with another aspect of the present disclosure, a surgical access device includes a cannula assembly, a fixation sleeve assembly, and a tip portion. The cannula assembly includes a housing and a tubular member extending from the housing. The cannula assembly defines a passage channel configured to receive a surgical instrument therethrough. The fixation sleeve assembly is slidably disposed about the tubular member of the cannula assembly. The fixation sleeve assembly includes a sleeve and a positioning member configured to fix a position of the sleeve relative to the tubular member of the cannula assembly. The tip portion is detachably coupled to a distal portion of the tubular member of the cannula assembly to retain the fixation sleeve assembly on the tubular member of the cannula assembly. The positioning member of the fixation sleeve assembly is movable between a first position, in which, the sleeve of the fixation sleeve assembly is in a tubular configuration and a second position, in which, the sleeve flexes radially outwards to define a fixation anchor configured to engage tissue to secure the surgical access device relative to an opening in tissue.

In an aspect, the positioning member of the fixation sleeve assembly in the first position may be disposed in a proximal portion of the tubular member of the cannula assembly.

In another aspect, the tubular member of the cannula assembly may include proximal and distal portions defining respective circumferential grooves.

In yet another aspect, the positioning member of the fixation sleeve may include an inner rim configured to be received in the circumferential grooves of the tubular member of the cannula assembly to fix the sleeve of the fixation sleeve assembly relative to the tubular member of the cannula assembly.

In still yet another aspect, the inner rim of the positioning member of the fixation sleeve may be formed of a resilient material.

In still yet another aspect, the positioning member and the sleeve of the fixation sleeve assembly may be integrally formed as a single construct.

In an aspect, the tip portion may be threadably coupled to the cannula assembly.

In another aspect, the fixation anchor may have a tapered or conical configuration.

In yet another aspect, the tip portion may have an outer diameter greater than an inner diameter of the sleeve.

BRIEF DESCRIPTION OF THE DRAWINGS

Various aspects of the present disclosure are illustrated herein with reference to the accompanying drawings, wherein.

DETAILED DESCRIPTION

Figure 1:
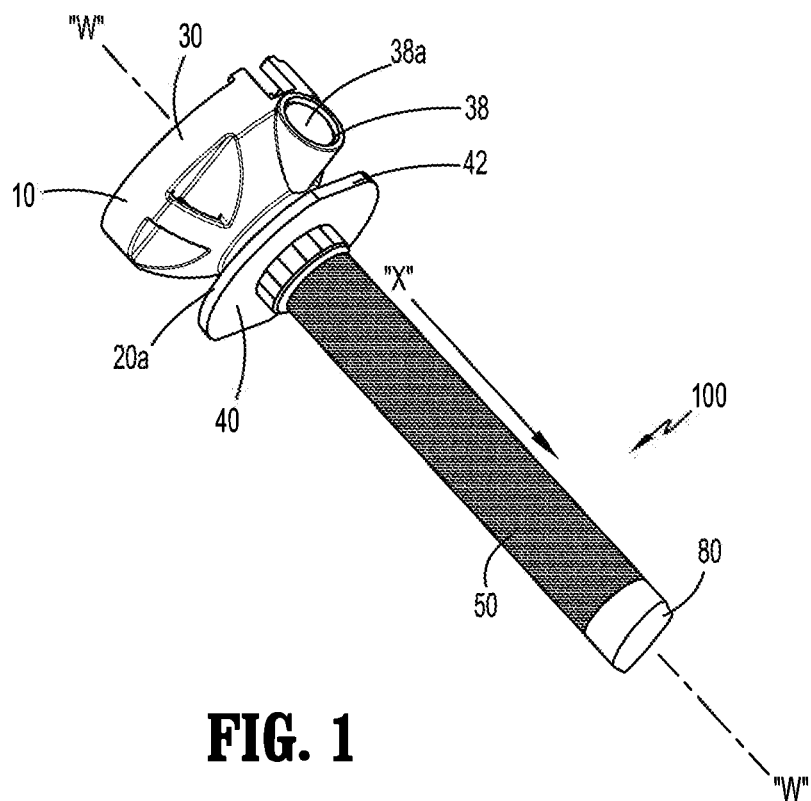
FIG. 1 is a perspective view of a surgical access device in accordance with the present disclosure.

The presently disclosed surgical access devices are described in detail with reference to the drawings, wherein like reference numerals designate corresponding elements in each of the several views. However, it is to be understood that the disclosed devices are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure. As used herein, the term "distal" refers to that portion of the instrument, or component thereof which is farther from the user while the term "proximal" refers to that portion of the instrument or component thereof which is closer to the user.

Referring initially to FIG. 1, there is illustrated a surgical access device 100 in accordance with the present disclosure. The surgical access device 100 is configured to permit access to an insufflated abdominal cavity during a laparoscopic procedure to permit the introduction of a surgical instrument for performing various surgical tasks on internal organs within the cavity. The surgical instrument may include laparoscopic or endoscopic clip appliers, graspers, dissectors, retractors, staplers, laser probes, photographic devices, tubes, endoscopes and laparoscopes, electro-surgical devices and the like.

Figure 2:
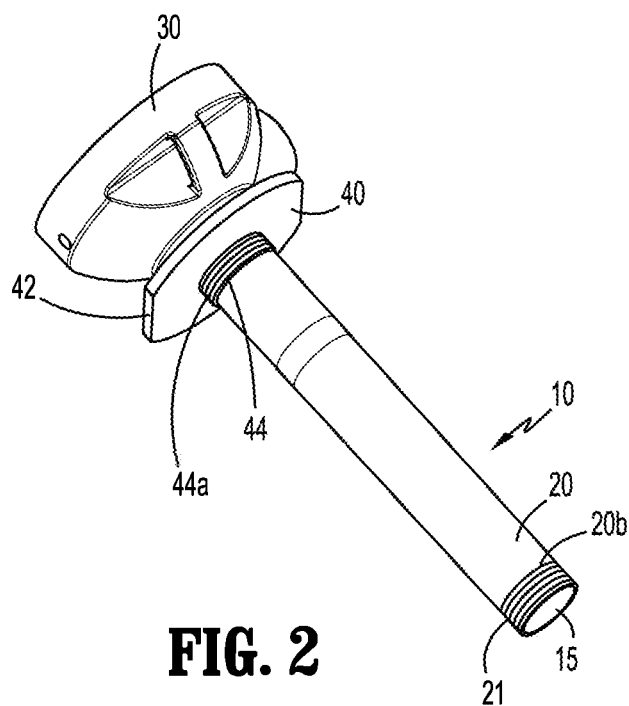
FIG. 2 is a perspective view of a cannula assembly of the surgical access device of FIG. 1.

With reference to FIGS. 1-4, the surgical access device 100 includes a cannula assembly 10, a locking collar 40 slidably mounted on the cannula assembly 10, a fixation sleeve assembly 50 selectively coupled with the locking collar 40 and transitionable to be anchored against tissue, and a tip portion 80 detachably securable to the cannula assembly 10. With particular reference to FIG. 2, the cannula assembly 10 includes a tubular member 20 defining a longitudinal channel passage 15 configured for reception and passage of a surgical instrument therethrough, and a housing 30 that may be integrally formed or detachably coupled with the tubular member 20. The tubular member 20 may be attached to the housing 30 using known techniques such as RF welding, ultrasonic welding, adhesives, etc. It is further contemplated that the tubular member 20 and the housing 30 may be molded as a single construct.

The housing 30 has open proximal and distal ends defining a cavity therein. The housing 30 may include one or more seals including, e.g., an object seal dimensioned to establish a sealed relationship about the surgical instrument introduced therein, and a zero closure valve adapted to open to permit passage of the surgical instrument and close in the absence of the surgical instrument to inhibit loss of insufflation gases. For a detailed description of the structure and function of exemplary seal assemblies, reference may be made to U.S. Pat. No. 10,022,149, the entire contents of which are hereby incorporated by reference. The housing 30 further includes a port 38 defining an opening 38a therethrough and an associated valve (not shown) for coupling to a source of insufflation for introducing gases within the longitudinal channel passage 15 of the tubular member 20 for distribution within the abdominal cavity during the laparoscopic procedure. The valve has a lever that is rotatable about an axis of the valve enabling the user to open and close the valve. The lever may be positioned in one of a plurality of intermediate positions allowing the user to adjust the flow rate of a fluid through the valve.

The components of the surgical access device 100 may be formed from suitable biocompatible materials such as medical grade metals (e.g., stainless steel, titanium or aluminum), polymeric materials (e.g., polycarbonate), or combinations thereof. The cannula assembly 10 may be opaque, for example radio opaque, translucent or transparent in whole or in part. The access device 100 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, the cannula assembly 10 may be configured as a cleanable/sterilizable, reusable component, while the fixation sleeve assembly 50 is configured as a single-use, disposable/reprocessable component. To this end, the fixation sleeve assembly 50 is configured to be releasably coupled to the cannula assembly 10 to facilitate disposal/reprocessing of any single-use components and cleaning and/or sterilization of any reusable components.

Figure 4:
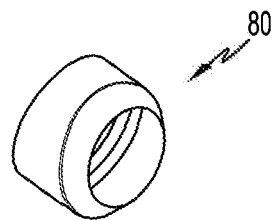
FIG. 4 is a perspective view of a tip portion of the surgical access device of FIG. 1.

With particular reference to FIGS. 1 and 2, the tubular member 20 of the cannula assembly 10 includes proximal and distal portions 20a, 20b defining respective openings configured to receive a surgical instrument therethrough. The opening of the proximal portion 20a is in communication with the housing 30. The proximal portion 20a of the tubular member 20 includes a proximal retaining feature to retain the locking collar 40 thereon. The proximal retaining feature may frictionally support the locking collar 40 in place. For example, an outer diameter of the proximal portion 20a of the tubular member 20 and/or an inner diameter of the locking collar 40 may be chosen to enhance frictional contact therebetween. The locking collar 40 may include an inner rim (not shown) formed of resilient material and configured to be received in a circumferential groove defined in the proximal portion 20a of the tubular member 20. The distal portion 20b of the tubular member 20 may also include a distal retaining feature configured to retain the locking collar 40 thereon. For example, an outer diameter of the distal portion 20b of the tubular member 20 and/or the inner diameter of the locking collar 40 may be chosen to frictionally retain the locking collar 40 on the distal retaining feature. In addition, the distal portion 20b includes a threaded portion 21 configured to threadably engage the tip portion 80 (FIG. 4). It is also envisioned that the tubular member 20 may further include a rib (not shown) configured to create a controlled interference with an inner surface of the locking collar 40 such that the locking collar 40 may be retained along the tubular member 20.

With continued reference to FIGS. 1 and 2, the locking collar 40 is configured to be slidably supported about the tubular member 20 of the cannula assembly 10. In particular, the locking collar 40 includes an annular base 44 having threads 44a on an outer surface thereof, and an annular flange portion 42 extending radially outward from the annular base 44. In addition, the annular flange portion 42 is located proximal of the threads 44a of the annular base 44.

Figure 3:
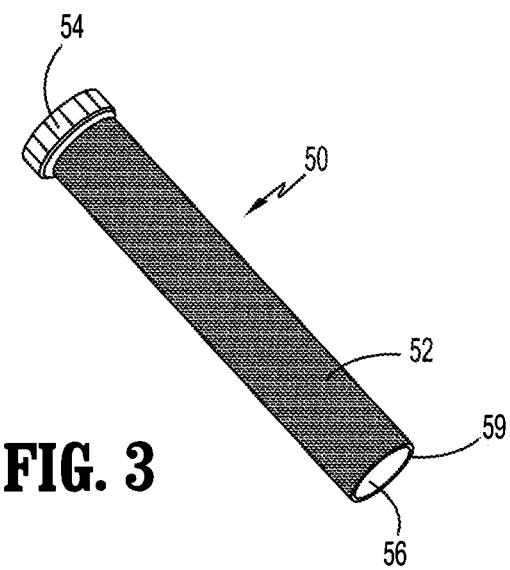
FIG. 3 is a perspective view of a fixation sleeve assembly of the surgical access device of FIG. 1.

With reference now to FIG. 3, the fixation sleeve assembly 50 includes a tubular sleeve 52 formed of a flexible material to flex radially outwards. The tubular sleeve 52 may be formed of a material to provide a sealing relation with tissue. The tubular sleeve 52 defines a lumen 56 configured to receive the tubular member 20 of the cannula assembly 10 therethrough. The fixation sleeve assembly 50 further includes a nut 54 coupled to the tubular sleeve 52. The nut 54 has an inner surface having threads configured to threadably engage the threaded portion 44a of the locking collar 40 to enable selectively detachable coupling of the fixation sleeve assembly 50 with the locking collar 40. The tubular member 20 of the cannula assembly 10 may be longer than the fixation sleeve assembly 50, and thus, extend beyond a distal portion 59 of the fixation assembly 50. The tubular sleeve 52 may include a braid, a weave, a mesh, a nonwoven structure, a knitted structure, a fabric or the like. The tubular sleeve 52 incorporates a braided fabric including strands of natural and/or synthetic materials including cotton, silk, polyethylene, polypropylene, polyethylene, nylon, polyamides, polyglycolic acid, polyethylene teraphthalate (PET), glycolide-lactide copolymer, poly aryl ether-ether ketone, etc. and/or a combination of these strands. Metal strands, such as stainless steel, MP35N, nitinol and/or Titanium may also be used to form the tubular sleeve. An elastomeric material may be mounted to, formed on, or otherwise applied to the tubular sleeve 52, for example by dip molding or overmolding.

With reference to FIG. 4, the tip portion 80 is configured to be detachably coupled to the distal portion 20b of the tubular member 20 of the cannula assembly 10. The tip portion 80 has an inner surface including threads configured to threadably engage the threaded portion 21 of the distal portion 20b of the tubular member 20. The tip portion 80 may have an outer diameter greater than an inner diameter of the tubular sleeve 52 such that the tip portion 80 serves as a stop to retain the tubular sleeve 52 on the tubular member 20 of the cannula assembly 10. Alternatively, the tip portion 80 may be angled such that diametrically opposing portions of the tip portion 80 have different lengths from the proximal-most portion of the tip portion 80.

Figure 3A:
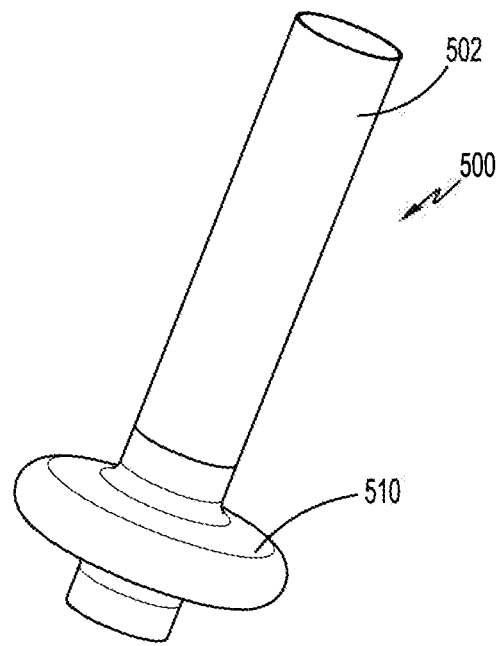
FIG. 3A is a perspective view of a protective sheath for use with the surgical access device of FIG. 1.
Figure 5:
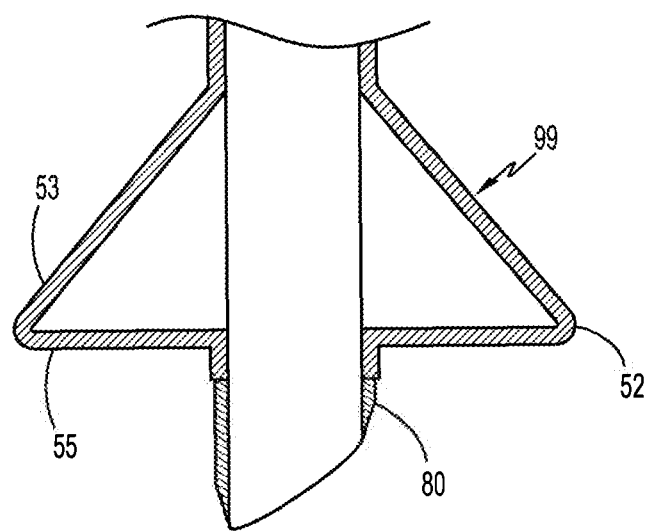
FIG. 5 is a partial cross-sectional view of the surgical access device of FIG. 1, illustrating a tubular sleeve of the fixation sleeve assembly defining a fixation anchor.

With reference to FIG. 5, the tubular sleeve 52 is transitionable to serve as a fixation anchor 99 to enhance securement of the surgical access device 100 relative to an opening in tissue. In particular, the tubular sleeve 52 is deployable between a tubular configuration corresponding to the locking collar 40 disposed in the proximal portion 20a of the tubular member 20 (FIG. 1), and an anchoring configuration in which the locking collar 40 is disposed adjacent the tip portion 80 such that the tubular sleeve 52 forms a fixation anchor 99. The anchoring configuration may be effected by advancing the annular flange portion 42 (FIG. 2) in a distal direction in the direction of an arrow "X" (FIG. 1) with sufficient force to overcome the resistance provided by the proximal retaining feature, while anchoring the distal portion 59 (FIG. 3) of the tubular sleeve 52 against the tip portion 80 accessing the abdominal cavity. As the annular flange portion 42 is advanced distally, the tubular sleeve 52 flexes outwardly to form the fixation anchor 99 including a lateral segment 53 and a distal segment 55. In order to facilitate flexing of the tubular sleeve 52 at a particular point along the length of the tubular sleeve 52, a sheath 500 (FIG. 3A) may be utilized. The tubular sleeve 52 is configured to be received within the sheath 500. The sheath 500 includes a tubular portion 502 and a balloon portion 510 extending radially outward from the tubular portion 502. The balloon portion 510 is configured to facilitate outward flexing of the tubular sleeve 52 therein when the annular flange portion 42 is advanced distally. The balloon portion 510 may be tailored to the surgical procedure being performed. For example, a sheath may include a balloon portion that is larger than the balloon portion 510 of the sheath 510 in order to create a larger anchoring configuration. The sheath 500 is also configured to protect tissue from trauma caused by the fixation sleeve assembly 50. It is also envisioned that a sheath may only include a tubular portion without a balloon portion. Under such a configuration, the sheath may be shorter in length than the tubular sleeve 52 such that the tubular sleeve 52 flexes outwardly adjacent a distal end of the sheath.

The lateral and distal segments 53, 55 define an umbrella shape which may further enhance securement of the fixation anchor 99 relative to tissue. The umbrella profile of the anchor secures the surgical access device 100 within the abdominal cavity and substantially minimizes any tendency of the surgical access device 100 to migrate from the cavity even when exposed to the pressurized environment of the pneumoperitoneum. The umbrella profile also occupies minimal space in the cavity to permit unencumbered introduction and manipulation of surgical instruments. The umbrella profile of the fixation anchor 99 will resist retropulsion of the portal relative to the abdominal cavity while accommodating multiple manipulations of the surgical instrument. For example, the tapered or conical segment of the fixation anchor 99 may reside or engage the incision in the abdominal wall and minimize loss of insufflation gases or blood.

In the anchoring configuration, the annular flange portion 42 rests with the distal retaining feature to resists movement of the fixation sleeve assembly 50 relative to the tubular member 20 of the cannula assembly 10, thereby maintaining the fixation anchor 99 in the anchoring configuration. The tubular sleeve 52 may be returned to the tubular configuration by exerting, e.g., a proximal force, on the annular flange portion 42, sufficient to cause the tubular sleeve 52 to revert back to the tubular profile and for the annular flange portion 42 to engage the proximal retaining feature of the tubular member 20.

The lateral and distal segments 53, 55 may be substantially planar and also may extend in orthogonal relationship with respect to the longitudinal axis "W-W" (FIG. 1) when the tubular sleeve 52 is in the expanded condition. The lateral and distal segments 53, 55 also may be in superposed relation, and possibly, in contacting relation, when in the anchoring configuration. The planar and superposed orientation of the anchor reduces the overall profile of the anchor within the abdominal cavity while also providing a substantially large surface area to resist withdrawal or retropulsion of the surgical access device 100 relative to the tissue site. In addition, the superposed or layered relationship of the lateral and distal segments 53, 55 increases the strength and stability of the fixation anchor thereby further resisting withdrawal of the surgical access device 100. The planar orientation of the anchor in the expanded condition may be made possible through the configuration of the tubular sleeve 52, e.g., through the weave or braid orientation, which is flexible to permit outward deflection with minimal effort on behalf of the clinician. The fixation anchor helps to form a seal, inhibiting blood loss from the incision.

The operation of the surgical access device 100 will now be discussed. Initially, the locking collar 40 is slidably received about the tubular member 20 of the cannula assembly 10. In particular, the locking collar 40 is supported on the proximal retaining feature of the tubular member 20 at the proximal portion 20a of the tubular member 20. The tubular member 20 is received through the lumen 56 of the tubular sleeve 52, and the nut 54 of the fixation sleeve assembly 50 is threadably coupled to the threaded portion 44a of the locking collar 40. Once fixation sleeve assembly 50 is secured with the locking collar 40 such that the fixation sleeve assembly 50 and the locking collar 40 are movable as a single construct, the tip portion 80 is coupled with the distal portion 20b of the tubular member 20. Under such a configuration, the fixation sleeve assembly 50 is slidably secured to the tubular member 20.

With the locking collar 40 disposed in the proximal retaining feature corresponding to the tubular configuration of the tubular sleeve 52 (FIG. 1), an obturator (not shown) is positioned within the surgical access device 100 and advanced such that its penetrating end extends beyond the opening of the distal end 20b of the tubular member 20. The obturator is used to penetrate the abdominal wall as is conventional in the art, and the obturator is thereafter removed leaving the surgical access device 100 in position accessing the abdominal cavity. When it is desired to expand the tubular sleeve 52 to define the fixation anchor 99, the annular flange portion 42 may be advanced relative to the tubular member 20 by exerting a downward force on the annular flange portion 42 to cause the tubular sleeve 52 to transition to its anchoring configuration (FIG. 5) engaging the internal surface of the abdominal wall. Specifically, once the tip portion 80 is inserted in the opening in tissue, the clinician may push the annular flange portion 42 to displace the locking collar 40 distally until the annular flange portion 42 engages the distal retaining feature to secure the annular flange portion 42 adjacent the tip portion 80, while the distal portion of the tubular sleeve 52 is anchored against the tip portion 80. In this manner, the tubular sleeve 52 extends radially outwardly within the opening in tissue such that the tubular sleeve 52 engages the inner surface of tissue to provide fixation of the surgical access device 100 in the opening in tissue. In laparoscopic surgery, the peritoneal or abdominal cavity is insufflated to raise the cavity wall to establish a pneumoperitoneum and provide greater access to the tissue and organs within the cavity. At this time, a fluid such as a cleaning fluid, an insufflation fluid (e.g., $CO_2$), sterile saline, a surfactant solution, may be supplied through the lumen of the tubular member 20 via the port 38 of the housing 30. Surgical instruments may be inserted through the lumen of the housing 30 and the tubular member 20 to direct the surgical instrument toward the surgical site.

When it is desired to remove the surgical access device 100, the annular flange portion 42 is retracted to permit relative movement of the tubular sleeve 52 to the proximal position causing the tubular sleeve 52 to transition to the tubular configuration. The surgical access device 100 is thereafter removed from the patient. At this time, the fixation sleeve assembly 50 may be separated from cannula assembly 10 and discarded, while the cannula assembly 10 and the tip portion 80 may be sterilized for reuse.

The surgical access device 100 and the associated fixation anchor is highly effective in providing a secure portal for introduction of a surgical instrument. However, the cannula assembly 10 (FIG. 2) of the surgical access device 100 may be utilized as a standalone device without the fixation sleeve assembly 50 (FIG. 3).

Figure 6:
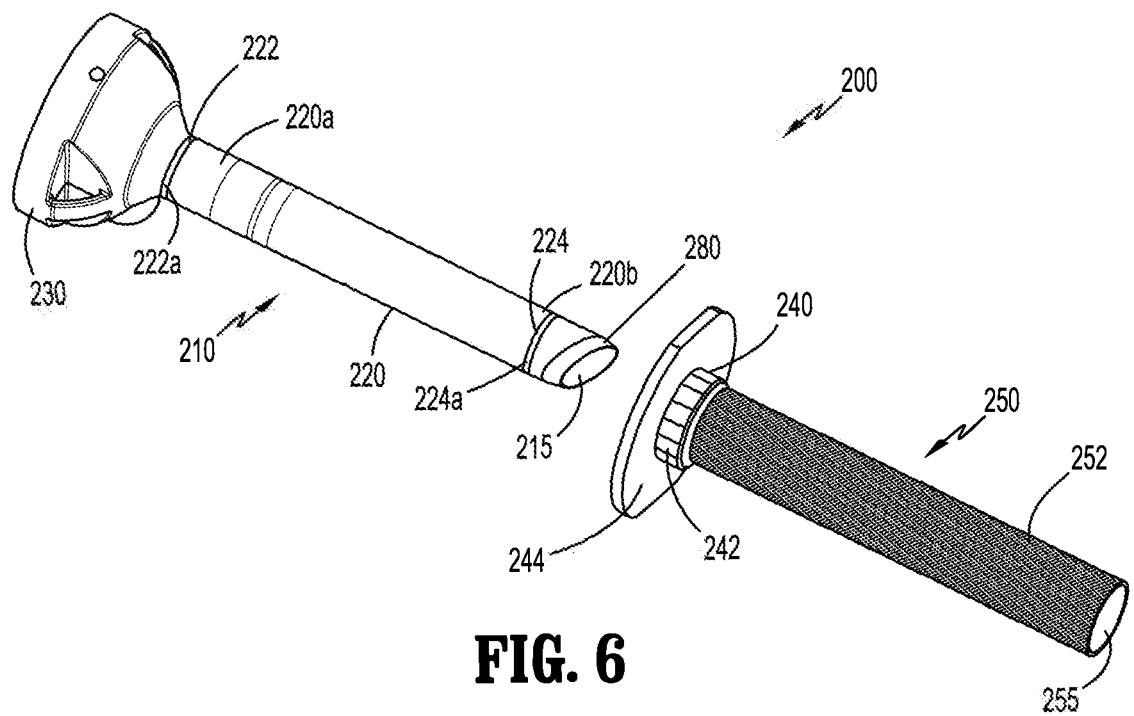
FIG. 6 is a perspective view of a surgical access device in accordance with the present disclosure, with a fixation sleeve assembly separated from a cannula assembly.
Figure 7:
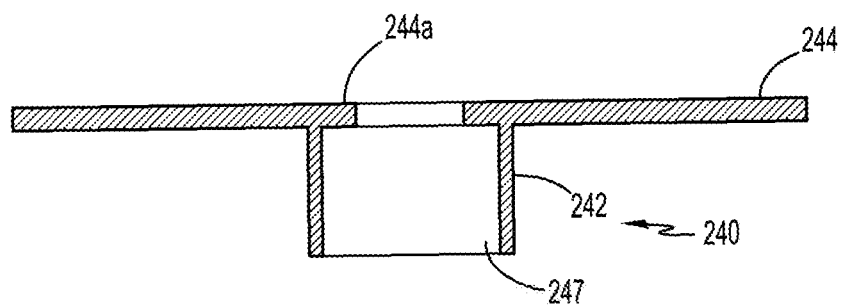
FIG. 7 is a side cross-sectional view of a locking collar of the fixation sleeve assembly of FIG. 6.

With reference now to FIG. 6, a surgical access device in accordance with the present disclosure is generally shown as a surgical access device 200. Parts of the surgical access device 200 substantially similar to the parts of the surgical access device 100 will not be described herein to avoid obscuring the present disclosure in unnecessary detail. The surgical access device 200 includes the cannula assembly 210, a fixation sleeve assembly 250 selectively coupled with the cannula assembly 210 and transitionable to be anchored against tissue, and a tip portion 280 detachably secured with the cannula assembly 210. The cannula assembly 210 includes a tubular member 220 defining a longitudinal channel passage 215 configured for reception and passage of a surgical instrument therethrough, and a housing 230 that may be integrally formed or detachably coupled with the tubular member 220. The housing 230 may include seals and a port, as described hereinabove. The components of the surgical access device 200 may be formed from suitable biocompatible materials such as medical grade metals (e.g., stainless steel, titanium or aluminum), polymeric materials (e.g., polycarbonate), or combinations thereof. The access device 200 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, the cannula assembly 210 may be configured as a cleanable/sterilizable, reusable component, while the fixation sleeve assembly 250 is configured as a single-use, disposable/reprocessable component. To this end, the fixation sleeve assembly 250 is configured to releasably engage the cannula assembly 210 to facilitate disposal/reprocessing of any single-use components and cleaning and/or sterilization of any reusable components. In addition, the housing 230 may be configured as a single-use device and the tubular member 220 may be configured for sterilized for re-use.

The tubular member 220 of the cannula assembly 210 includes proximal and distal portions 220a, 220b having respective proximal and distal retaining features 222, 224. The proximal and distal retaining features 222, 224 define respective circumferential grooves 222a, 224a. It is contemplated that the circumferential grooves 222a, 224a may be positioned along the length of the cannula assembly 210. In addition, the distal portion 220b may include threaded portion (not shown) to threadably support the tip portion 280, as discussed hereinabove. The tip portion 280 may be detachably secured to the tubular member 220 via friction fit or snap fit, etc.

The fixation sleeve assembly 250 includes a tubular sleeve 252 defining a channel 255 configured to receive a surgical instrument therethrough, and a locking collar 240 coupled to the tubular sleeve 252. The locking collar 240 includes an annular base 242 and an annular flange 244 extending radially outwards from the annular base 242. Further, the locking collar 240 defines a channel 247 therethrough. The locking collar 240 may be integrally or monolithically formed. In particular, the annular flange 244 includes an inner portion 244a extending radially inward into the channel 247 of the locking collar 240. The inner portion 244a may be formed of resilient material to enable flexing for selective securement within the circumferential grooves 222a, 224a of the proximal and distal retaining features 222, 224 of the tubular member 220. For example, when the clinician applies sufficient axial force to the annular flange 244, the inner portion 244a of the annular flange 244 may be placed into the circumferential groove 222a, 224a or displaced from the circumferential groove 222a, 224a. It is further contemplated that a distal portion of the tubular sleeve 252 may be coupled to the tip portion 280 by, e.g., snap fit or threadable configuration. Under such a configuration, the locking collar 240 may selectively secure the fixation sleeve assembly 250 to the proximal or distal portions 220a, 220b of the tubular member 220 of the cannula assembly 210. As discussed hereinabove with respect to fixation sleeve assembly 50, the tubular sleeve 252 may be formed of a flexible material to flex radially outwards. The tubular sleeve 252 may be formed of a material to provide a sealing relation with tissue.

The tip portion 280 is configured to be detachably coupled to the distal portion 220b of the tubular member 220 of the cannula assembly 210. The tip portion 280 has an inner surface including threads configured to threadably engage the threaded portion of the distal portion 220b of the tubular member 220. The tip portion 280 may have an outer diameter larger than an inner diameter of the tubular sleeve 252 such that the tip portion 280 serves as a stop to retain the tubular sleeve 252 on the tubular member 220.

The tubular sleeve 252 is selectively transitionable to form a fixation anchor as described hereinabove. The tubular sleeve 252 is transitionable between a tubular configuration, in which, the inner portion 244a of the locking collar 240 engages the proximal retaining portion 222, i.e., the circumferential groove 222a, and an anchoring configuration, in which, the inner portion 244a of the locking collar 240 engages the distal retaining portion 224, i.e., the circumferential groove 224a, such that the tubular sleeve 252 flexes outwardly to define a fixation anchor having, e.g., an umbrella configuration, as described hereinabove with respect to the tubular sleeve 52. Such a configuration facilitates securement of the anchor relative to the tissue. The tubular sleeve 252 is displaced to the anchoring configuration by moving, e.g., the annular flange 244, in a distal direction with sufficient force to overcome the resistance provided by the proximal retaining feature 222. In the anchoring configuration, the inner portion 244a of the annular flange 244 rests within the distal retaining feature 224 to resists relative movement of the fixation sleeve assembly 250 and the tubular member 220 of the cannula assembly 210, thereby maintaining the fixation anchor in the anchoring configuration.

For example, the tapered or conical segment of the expanded anchor segment may reside or engage the incision in the abdominal wall and minimize loss of insufflation gases or blood. The tubular sleeve 252 may be returned to the first position by exerting, e.g., a proximal force, on the annular flange 244, sufficient to cause the tubular sleeve 252 to revert back to the tubular profile and for the annular flange 244 to engage the proximal retaining feature 222 on the tubular member 220. It is contemplated that the surgical access device 200 may be used as a standalone cannula assembly 210 or as a cannula assembly 210 having a fixation feature, i.e., the fixation sleeve assembly 250 configured to facilitate securement of the cannula assembly 210 to a patient. The use of the surgical access device 200 is substantially similar to the use of the surgical access device 100 and thus will not be described herein.

Persons skilled in the art will understand that the devices and methods specifically described herein and illustrated in the accompanying drawings are non-limiting and exemplary. It is envisioned that the elements and features illustrated or described in connection with one example may be combined with the elements and features of another without departing from the scope of the present disclosure. While the device has been particularly shown and described, it will be understood by those skilled in the art that various modifications and changes in form and detail may be made therein without departing from the scope and spirit of the disclosure. For example, the fixation anchor may be pre-formed to any number of shapes including spheroid, oval, rectangular, conical or the like. The fixation anchor may be elliptical or oval in configuration when in the anchoring configuration. Accordingly, the above description should not be construed as limiting. Thus, modifications such as those suggested above, but not limited thereto, are to be considered within the scope of the disclosure.

The invention claimed is:

1. A surgical access device comprising:
    a cannula assembly including a housing and a tubular member extending from the housing, the cannula assembly defining a passage channel configured to receive a surgical instrument;
    a locking collar slidably received on the tubular member of the cannula assembly, the locking collar having an annular base and an annular flange extending radially outward from the annular base and proximal of the annular base;
    a fixation sleeve assembly disposed about the tubular member of the cannula assembly, the fixation sleeve assembly operably coupled to the locking collar, and a sleeve extending distally from the locking collar, the fixation sleeve assembly including a securing member that threadably engages threads on an outer surface of the annular base; and
    a tip portion extending from and detachably coupled to a distal portion of the tubular member of the cannula assembly to retain the fixation sleeve assembly on the tubular member of the cannula assembly,
    wherein the fixation sleeve assembly is transitionable between a first configuration, in which, the sleeve has a tubular profile, and a second configuration, in which, the sleeve flexes radially outwards to define a fixation anchor configured to secure the surgical access device relative to an opening in tissue.

2. The surgical access device according to claim 1, wherein the locking collar is disposed in a proximal portion of the tubular member when the fixation sleeve assembly is in the first configuration, and in a distal portion of the tubular member when the fixation sleeve assembly is in the second configuration.

3. The surgical access device according to claim 1, wherein the tubular member of the cannula assembly includes a proximal retaining feature and a distal retaining feature to retain the locking collar.

4. The surgical access device according to claim 3, wherein the proximal retaining feature and the distal retaining feature frictionally engage the locking collar.

5. The surgical access device according to claim 3, wherein the distal retaining feature is disposed adjacent the tip portion.

6. The surgical access device according to claim 1, wherein the fixation anchor has a tapered configuration.

7. The surgical access device according to claim 1, wherein the tip portion has an outer diameter greater than an inner diameter of the sleeve of the fixation sleeve assembly.

8. The surgical access device according to claim 1, wherein the sleeve of the fixation sleeve assembly includes a braid, a weave, a mesh, a non-woven structure, a knitted structure, or a fabric.

9. A surgical access device comprising:
a cannula assembly including a housing and a tubular member extending from the housing, the cannula assembly defining a passage channel configured to receive a surgical instrument, the tubular member including a proximal retaining feature and a distal retaining feature;
a fixation sleeve assembly slidably disposed about the tubular member of the cannula assembly, the fixation sleeve assembly including a sleeve and a positioning member configured to fix a position of the sleeve relative to the tubular member of the cannula assembly, the proximal retaining feature and the distal retaining feature configured to retain the positioning member by frictionally engaging the positioning member;
a securing member configured to detachably engage the positioning member, the securing member threadably engaging the positioning member; and
a tip portion extending from and detachably coupled to a distal portion of the tubular member of the cannula assembly to retain the fixation sleeve assembly on the tubular member of the cannula assembly,
wherein the positioning member of the fixation sleeve assembly is movable between a first position, in which, the sleeve of the fixation sleeve assembly is in a tubular configuration and a second position, in which, the sleeve flexes radially outwards to define a fixation anchor configured to engage tissue to secure the surgical access device relative to an opening in tissue.

10. The surgical access device according to claim 9, wherein the positioning member of the fixation sleeve assembly in the first position is disposed in a proximal portion of the tubular member of the cannula assembly.

11. The surgical access device according to claim 9, wherein the tip portion is threadably coupled to the cannula assembly.

12. The surgical access device according to claim 9, wherein the fixation anchor has a tapered or conical configuration.

13. The surgical access device according to claim 9, wherein the tip portion has an outer diameter greater than an inner diameter of the sleeve.

* * * * *